United States Patent [19]

Jungbauer et al.

[11] Patent Number: 5,423,982
[45] Date of Patent: Jun. 13, 1995

[54] LIQUID CHROMATOGRAPHY COLUMN ADAPTED FOR IN SITU CHEMICAL STERILIZATION

[75] Inventors: Alois Jungbauer; Hans P. Lettner, both of Vienna, Austria

[73] Assignee: BioSepra Inc., Marlborough, Mass.

[21] Appl. No.: 251,847

[22] Filed: May 31, 1994

[51] Int. Cl.6 .............................................. B01D 15/08
[52] U.S. Cl. .................................... 210/198.2; 96/105
[58] Field of Search .................. 210/635, 656, 198.2, 210/282, 450, 456, 232, 238; 96/105

[56] References Cited

U.S. PATENT DOCUMENTS

| | | | |
|---|---|---|---|
| 3,474,908 | 10/1969 | Catravas | 210/282 |
| 3,487,938 | 1/1970 | Patterson | 210/198.2 |
| 3,966,609 | 6/1976 | Godbille | 210/198.2 |
| 4,350,595 | 9/1982 | Gunkel | 210/198.2 |
| 4,361,482 | 11/1982 | Teetz | 210/198.2 |
| 4,512,731 | 4/1985 | Cobb | 210/510.1 |
| 4,582,608 | 4/1986 | Ritacco | 210/198.2 |
| 4,636,315 | 1/1987 | Allen, Jr. | 210/198.2 |
| 4,769,141 | 9/1988 | Couillard | 210/198.2 |
| 4,797,209 | 1/1989 | Jackson | 210/198.2 |
| 4,861,473 | 8/1989 | Shackelford | 210/198.2 |
| 4,865,728 | 9/1989 | Larsson | 210/198.2 |
| 4,888,112 | 12/1989 | Kronwald | 210/198.2 |
| 4,891,133 | 1/1990 | Colvin | 210/198.2 |
| 4,894,152 | 1/1990 | Colvin | 210/198.2 |
| 4,927,531 | 5/1990 | Sakamoto | 210/198.2 |
| 5,137,628 | 8/1992 | Hart | 210/198.2 |
| 5,141,635 | 8/1992 | LePlang | 210/198.2 |
| 5,167,810 | 12/1992 | Vassarotti | 210/198.2 |
| 5,169,522 | 12/1992 | Shalon | 210/198.2 |
| 5,188,730 | 2/1993 | Kronwald | 210/198.2 |
| 5,268,097 | 12/1993 | Girot et al. | 210/198.2 |
| 5,366,621 | 11/1994 | Bidell | 210/198.2 |

OTHER PUBLICATIONS

Adner et al., "Biotechnology Product Validation, Part 3: Chromatography Cleaning Validation," BioPharm, pp. 44–48 (Apr., 1994).

*Primary Examiner*—Ernest G. Therkorn
*Attorney, Agent, or Firm*—Kriegsman & Kriegsman

[57] ABSTRACT

A liquid chromatography column well-suited for in situ sterilization effected by washing with a sterilization solution. In a preferred embodiment, the column comprises a liquid chromatography tube packed with a liquid chromatography resin. A piston assembly is mounted within the liquid chromatography tube towards the upper end thereof, the piston assembly including an upper portion and a lower portion, the lower portion being shaped to include a fluid distribution channel and a downwardly-extending collar, the downwardly-extending collar including an annular slot and defining an orifice in fluid communication with the fluid distribution channel. The column further includes a distributor for distributing fluid conducted through the fluid distribution channel over the entirety of the orifice, the distributor being positioned over the liquid chromatography resin and a corrugated expanding ring for mounting the distributor within the orifice, the corrugated expanding ring being mounted in the annular slot and serving to support the distributor. Preferably, the distributor is a metal plate, either in the form of a multilayer sintered metal filter, a perforated plate with a hole diameter less than the lower grain diameter of the resin particles, or a woven and/or sintered stainless steel monolayer welded onto a metal ring.

11 Claims, 9 Drawing Sheets

LIQUID CHROMATOGRAPHY COLUMN ADAPTED FOR IN SITU CHEMICAL STERILIZATION

FIELD OF THE INVENTION

The present invention relates generally to liquid chromatography columns and more particularly to a novel liquid chromatography column which is well-suited for in situ chemical sterilization.

BACKGROUND OF THE INVENTION

Liquid chromatography is one of the most powerful and commonly-used techniques available today for the separation of materials from solutions. Examples of materials removed from solution using liquid chromatography include proteins, viruses, nucleic acids, pyrogens, fine chemicals, food additives, drugs and the like. As can readily be appreciated, for many such applications, it is highly undesirable for any portion of the chromatography column to become colonized by and/or contaminated with microbes since such microbes may affect the purity of any material prepared using the column.

In response to this concern, rather elaborate steps have been taken in the past in an attempt to establish and maintain sterile conditions within chromatography columns. Such steps have included autoclaving and/or chemically sterilizing chromatography resins ex situ (this option being limited to those resins which are amenable to such forms of treatment), pre-sterilizing chromatography tubes and their associated parts by chemical, thermal and/or radiative means, packing chromatography resins into columns in environments of low germ concentration, and pre-sterilizing sample solutions and aseptically connecting them to the columns.

Despite the array of sterilization procedures mentioned above, the maintenance of sterile conditions in chromatography columns is difficult to achieve in practice because chromatography columns typically include one or more "dead spaces" wherein microbes have a tendency to become ensconced and which cannot readily be accessed in situ by washing the column with a suitable sterilization solution.

For example, referring to FIG. 1, there is shown a fragmentary, simplified, schematic, section view of a first type of conventional liquid chromatography column, the first conventional chromatography column being represented generally by reference numeral 11. Column 11, which may be, for example, a Sepracor UPSCALE TM chromatography column (Marlborough, Mass.), includes a glass chromatography tube 13 which is partially filled with a suitable chromatography resin (not shown). A piston assembly 15 comprising an upper portion 15-1 and a lower portion 15-2 is mounted inside the upper portion of tube 13. The outer peripheral edge 17 of lower portion 15-2 extends conically downwards and, in combination with the inside surface of tube 13 and upper portion 15-1, defines an annular space 19. A sealing ring 21 is positioned within space 19 and extends downwardly just beyond the bottom of lower portion 15-2.

Lower portion 15-2 of piston 15 is also shaped to include radial grooves 22, a centrally-located fluid distribution channel 23, and a downwardly-extending collar 24. Collar 24 is shaped to define a circular orifice 25 in fluid communication with channel 23 and includes a pair of annularly-shaped, spaced-apart slots 29 and 31.

An expanding ring 33 of resilient material is mounted in slot 29, and an O-ring 35 is mounted in slot 31. A polyethylene frit 37 (or gauze membrane), which is used both to distribute the liquid transmitted through channel 23 over the entirety of orifice 25 and to retain the resin in the column, is positioned across orifice 25 and is held in place between expanding ring 33 and O-ring 35.

As can be appreciated, numerous dead spaces not readily accessible to rapid liquid exchange using a sterilization solution are present in the areas where expanding ring 33 and O-ring 35 are joined to lower portion 15-2. Additional dead spaces are present in the areas between polyethylene frit 37 and expanding ring 33 and in the areas between polyethylene frit 37 and O-ring 35. Still further dead spaces are present within polyethylene frit 37, itself, which lacks well-defined pores for fluid flow.

Referring now to FIG. 2, there is shown a fragmentary, simplified, schematic, section view of a second type of conventional liquid chromatography column, the second conventional chromatography column being represented generally by reference numeral 51. Column 51 may be, for example, a BPG 100/500 BioProcess TM Glass Column chromatography column from Pharmacia (Uppsala, Sweden). Column 51 includes a glass chromatography tube 53 which is partially filled with a suitable chromatography resin (not shown). A piston assembly 55 comprising an upper portion 55-1 and a lower portion 55-2 is mounted inside the upper portion of tube 53. A sealing O-ring 57 is sandwiched between upper portion 55-1 and lower portion 55-2 of piston 55, O-ring 57 pressing against tube 53 and pressing upper and lower portions 55-1 and 55-2, respectively, of piston 55 together.

Lower portion 55-2 of piston 55 is shaped to include a centrally-located fluid distribution channel 63 which opens, at the base of lower portion 55-2, into a large orifice 65. A gauze membrane 67 is positioned over orifice 65 and is welded or glued onto a plastic ring 68 which, in turn, fits on a nut 69 mounted in lower portion 55-2. A rough net plastics disk 70 is positioned between piston 55-2 and membrane 67.

As can be seen, the fit of ring 68 on piston 55-2 creates a lot of dead spaces which cannot readily be accessed by washing the column with a sterilization solution. In addition, numerous dead spaces are present within membrane 67 and disk 70.

SUMMARY OF THE INVENTION

It is an object of the present invention to provide a novel liquid chromatography column.

It is another object of the present invention to provide a liquid chromatography column that overcomes at least some of the drawbacks associated with conventional liquid chromatography columns of the type described above.

It is yet another object of the present invention to provide a liquid chromatography column that is well-suited for in situ sterilization effected by washing the column with a liquid sterilization solution.

It is still yet another object of the present invention to provide a liquid chromatography column that has a minimal number of dead spaces not readily accessible to rapid liquid exchange.

Accordingly, in furtherance of the above and other objects to be described or to become apparent hereafter, a liquid chromatography column well-suited for in situ sterilization is hereinafter provided, said liquid chromatography column comprising in a first preferred embodiment (a) a liquid chromatography tube packed with a liquid chromatography resin; (b) a piston assembly mounted within said liquid chromatography tube towards the upper end thereof, said piston assembly including an upper portion and a lower portion, said lower portion being shaped to include a fluid distribution channel and a downwardly-extending collar, said downwardly-extending collar including an annular slot and defining an orifice in fluid communication with said fluid distribution channel; (c) a distributor for distributing fluid conducted through said fluid distribution channel over the entirety of said orifice, said distributor being positioned over said liquid chromatography resin; and (d) means for mounting said distributor within said orifice, said mounting means comprising a corrugated expanding ring mounted in said annular slot, said corrugated expanding ring supporting said distributor.

Preferably, the distributor is a metal plate, either in the form of a multilayer sintered metal filter (e.g., a 5-layer or 10-layer FUJIPLATE filter), a perforated plate with a hole diameter less than the lower grain diameter of the resin particles, or a woven and sintered stainless steel monolayer welded onto a metal ring.

In a second preferred embodiment, the mounting means comprises, instead of a corrugated expanding ring, a plurality of wedges press-fitted into the annular slot of the collar at desired locations, said wedges similarly being used to support said distributor. Preferred distributors are those described above in connection with the first preferred embodiment.

In a third preferred embodiment, a metal distributor of the type mentioned above is welded directly to the collar of the piston.

As can readily be appreciated, by eliminating the use of conventional expanding rings to support the distributor and/or by eliminating the use of polyethylene frits, the present invention substantially reduces a number of dead spaces present in chromatography columns and is, therefore, more sanitary.

Additional objects, features, aspects and advantages of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 3:
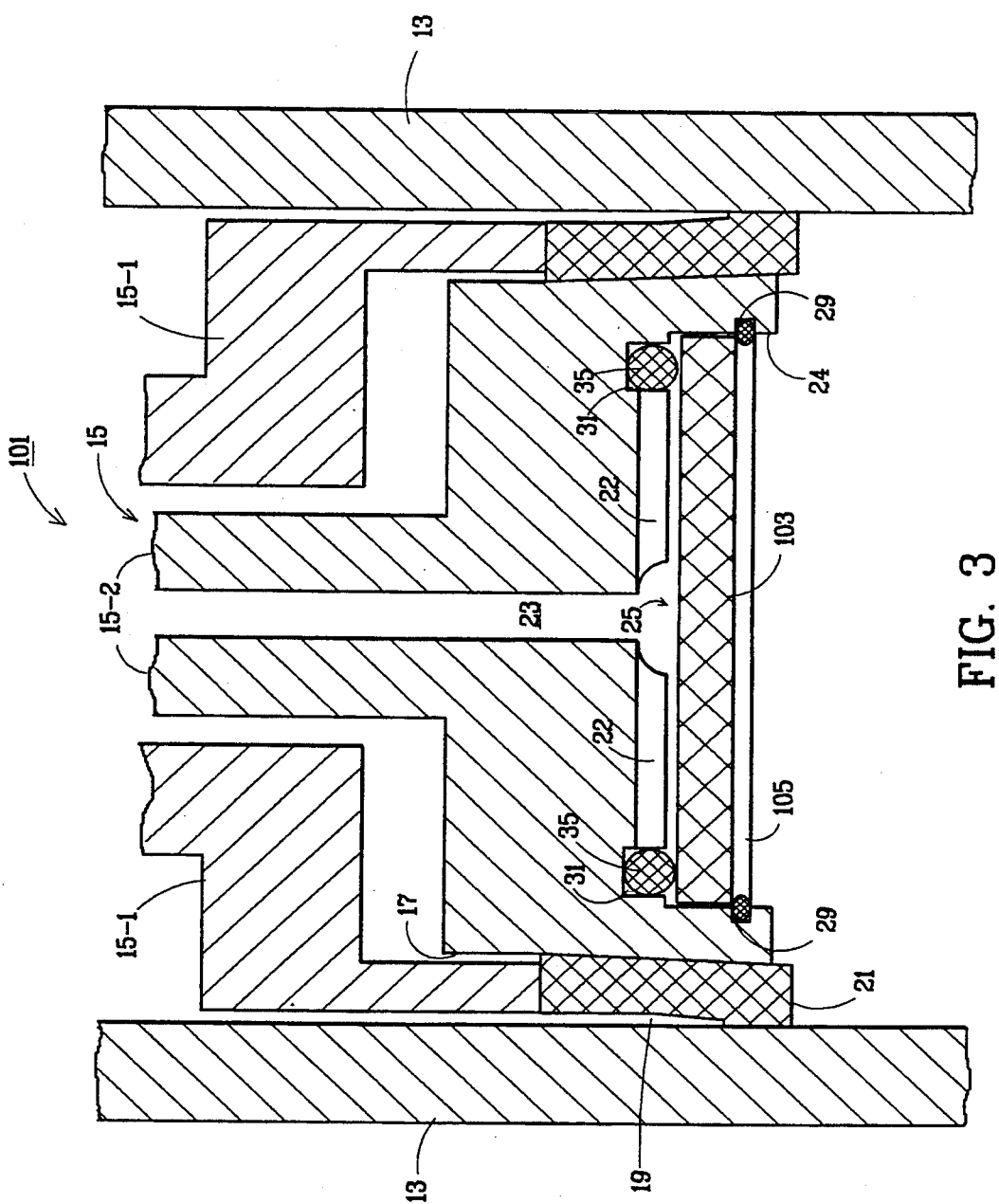
FIG. 3 is a fragmentary, simplified, schematic, section view of a first embodiment of a liquid chromatography column constructed in accordance with the teachings of the present invention.

Referring now to FIG. 3, there is shown a fragmentary, simplified, schematic, section view of a first embodiment of a liquid chromatography column constructed in accordance with the teachings of the present invention, said liquid chromatography column being well-suited for in situ sterilization and being represented generally by reference numeral 101.

Column 101 is very similar in construction to conventional chromatography column 11, the only differences between columns 11 and 101 being that column 101 includes (1) a multilayer sintered metal filter 103 as the distributor, instead of the polyethylene frit 37 included in column 11; and (2) a corrugated expanding ring 105 made of stainless steel, instead of the expanding ring 33 included in column 11.

Figure 4A:
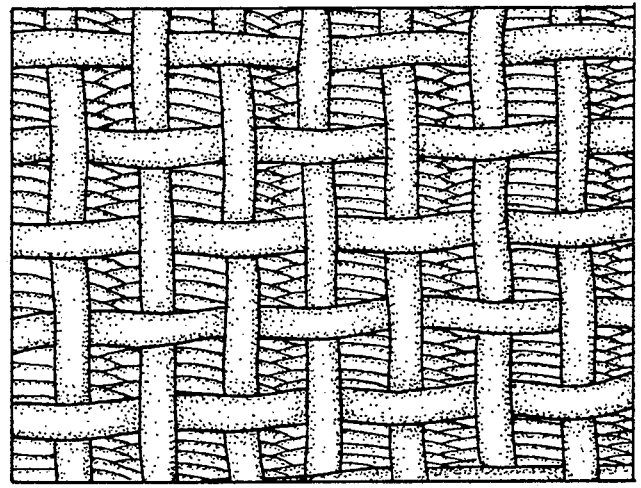
FIGS. 4(a) and 4(b) are top and section micrographs, respectively, of a portion of the fluid distributor shown in FIG. 3.
Figure 4B:
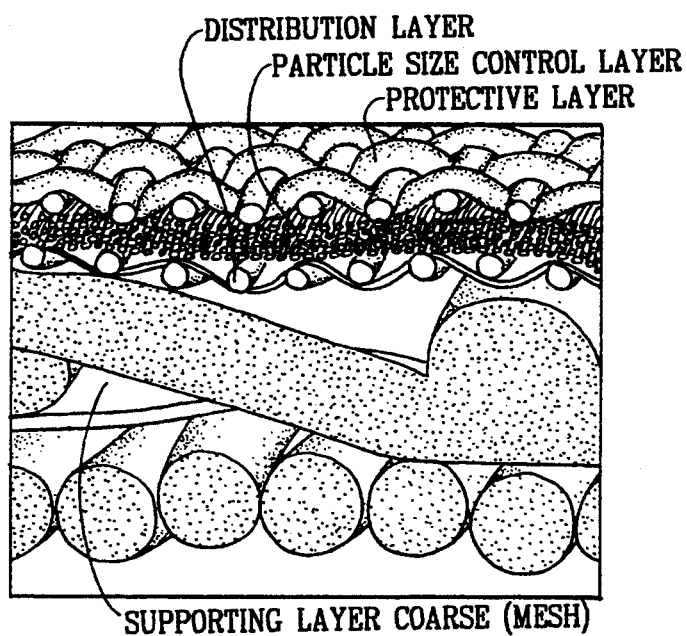

Referring now to FIGS. 4(a) and 4(b), there are shown top and section micrographs, respectively, of multilayer sintered metal filter 103. Filter 103 is commercially available, for example, from Fuji under the trade designation 5-layer FUJIPLATE disc type (Fuji Filter Manufacturing Co., Ltd, Tokyo, Japan). The aforementioned FUJIPLATE disc type is an integrated porous element made up of several layers of mesh sintered together. The sintering process used is based on maintaining metals at 90% of their melting point for a set period of time. Counter-diffusion of metal atoms at contact points and crystal formation is used to form a completely integrated metal structure. The inner mesh is of a very fine gauge and determines filter accuracy. It is overlaid with coarse support mesh layers. The material used to make the structure is typically stainless steel SUS 304, SUS 316. Hastelloy C-22 or C-276 can also be used. The filters are available in sizes from 2 mm to 2000 mm in diameter. Their void rate is 35%. Filtration readings reach from 0.5 to 200 μm. Operating temperatures range from -—269° C. to 480° C.

One advantage to using filter 103, as opposed to frit 37, is that filter 103 has a well-defined mesh with very few dead spaces in which microbes can become secluded from sterilizing solutions. Filter 103 serves to retain agglomerates of microbes while letting single cells pass through.

Figure 5:
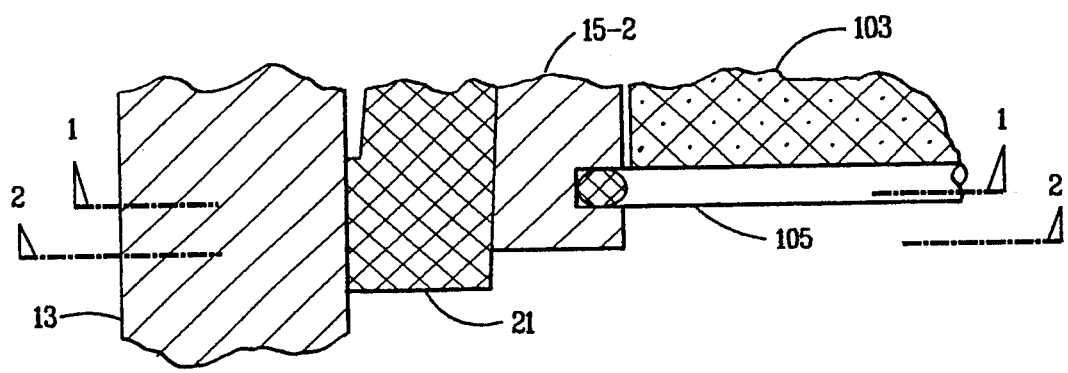
FIG. 5 is a top view of the corrugated expanding ring shown in FIG. 3.
Figure 6:
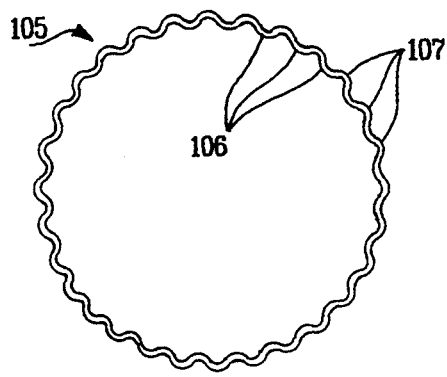
FIG. 6 is an enlarged, fragmentary, schematic, section view of the column of FIG. 1, illustrating the interrelation of the lower portion of the piston, the corrugated expanding ring and the fluid distributor.
Figure 7:
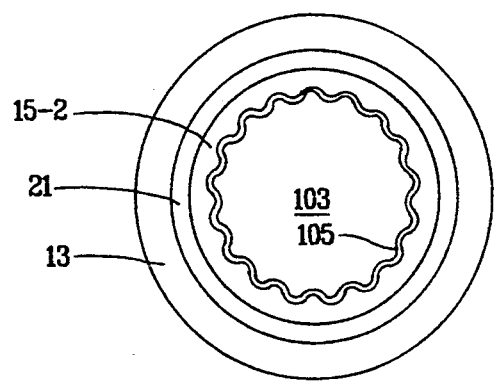
FIG. 7 is a simplified section view taken along line 1—1 of FIG. 5.
Figure 8:
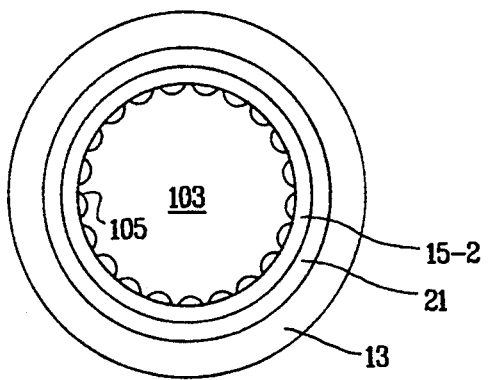
FIG. 8 is a simplified section view taken along line 2—2 of FIG. 5.

Referring now to FIG. 5, there is shown a top view of corrugated expanding ring 105. Ring 105 is corrugated in one plane so that it has inwardly extending teeth 106 adapted to engage slot 29 (see FIG. 6) and outwardly extending teeth 107 adapted to support filter 103 (see FIGS. 6 through 8). The number of teeth 106 and teeth 107 may vary. Because of the corrugated shape of ring 105, there are very few dead spaces in slot 29 which cannot readily be accessed by washing column 101 with a sterilization solution.

Figure 9A:
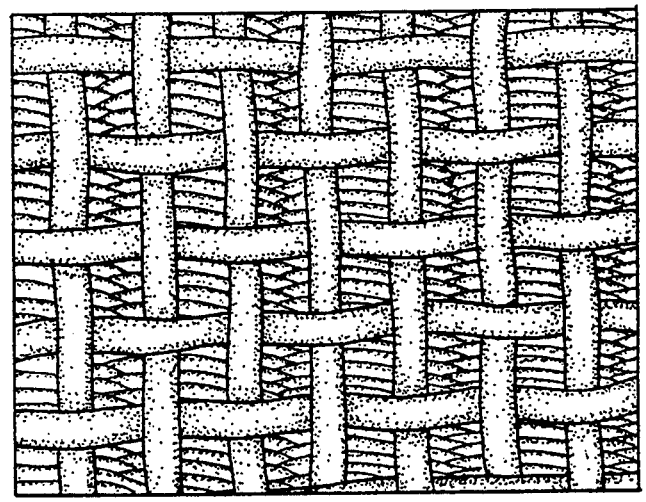
FIGS. 9(a) and 9(b) are top and section micrographs, respectively, of a portion of a second type of fluid distributor usable in the liquid chromatography column of FIG. 3.
Figure 9B:
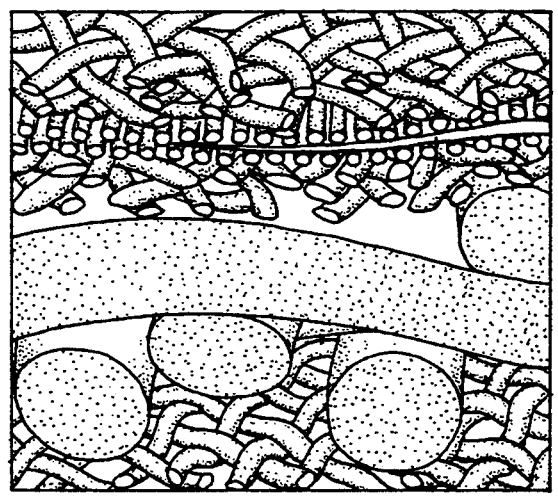

Referring now to FIGS. 9(a) and 9(b), there are shown top and section views, respectively, of a second type of multilayer sintered metal filter which may be used as the distributor in column 101, said multilayer filter being represented generally by reference numeral 111. Filter 111 is also available, for example, from Fuji Filter Manufacturing Co., Ltd. under the trade designation 10-layer FUJIPLATE disc type.

Figure 10:
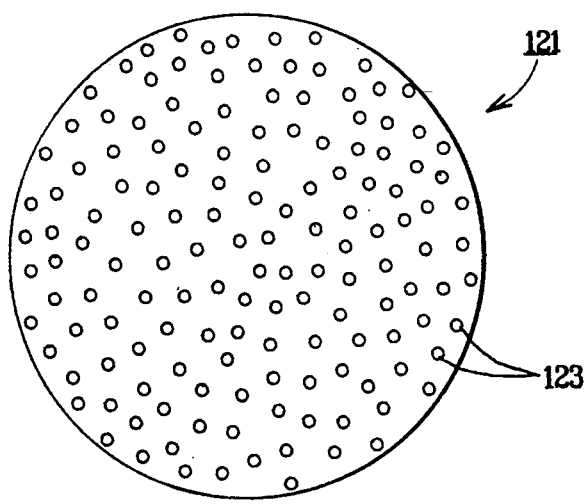
FIG. 10 is a top view of a third type of fluid distributor usable in the liquid chromatography column of FIG. 3.

Referring now to FIG. 10, there is shown a top view of a perforated metal plate which may be used as a third type of distributor in column 101, said perforated plate being represented generally by reference numeral 121. The perforations 123 in plate 121 have a hole diameter less than the lower grain diameter of the resin particles in the column. Plate 121 is a desirable distributor for purposes of the present invention because it offers a minimal number of dead spaces wherein microorganisms may become entrapped. To promote uniform flow distribution, especially in the case of shallow bed columns, it is necessary that resistance to flow across the perforated plate be of a significant magnitude. For a plate of a given thickness, the necessary value of resistance can be achieved either by a small number of large diameter holes or by a large number of small diameter holes. The latter case is preferred because a large number of small holes gives a local velocity distribution that is more uniform and because the smaller holes will allow the column to be used with a broader range of sorbent particle sizes. The manufacturing method chosen for a perforated plate will, in a practical sense, impose lower limits on hole diameter and upper limits on hole number. Examples of methods which could be used to perforate such plates include laser or acidic corrosion techniques.

Plate 121 may be, for example, a plate of stainless steel (304 SS or 316 SS) having perforations of about 0.5 to 200 μm.

Still another type of distributor usable in column 101 is a woven and/or sintered stainless steel monolayer (not shown). Woven steel nets are commercially available under the trade designation Duplex 15 at G. Bopp+Co. AG (Zurich, Switzerland). Except stainless steel, these can also be manufactured from nickel, argentan, copper, titan, Monel or Hastalloy. Preferably, such a monolayer is welded to a metal ring to provide the necessary rigidity thereto.

Figure 11:
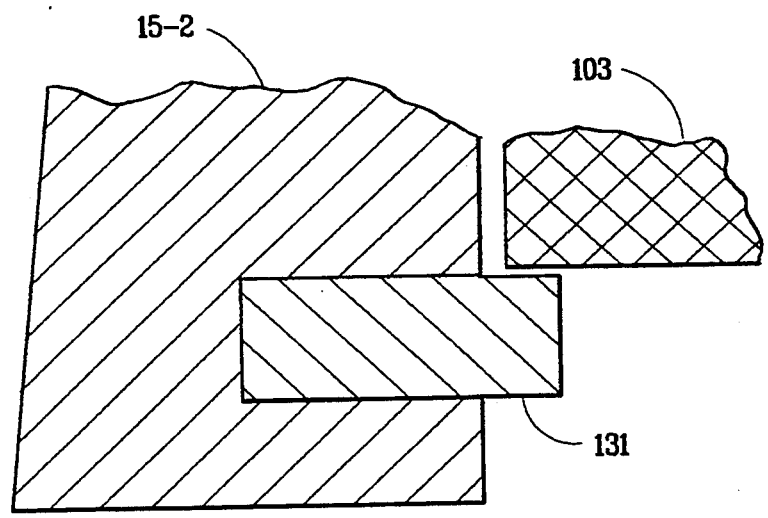
FIG. 11 is an enlarged, fragmentary, schematic, section view of an alternative arrangement to FIG. 6 for mounting the fluid distributor to the lower portion of the piston.

Referring now to FIG. 11, there is shown an enlarged, fragmentary, schematic, section view of an alternative arrangement to FIG. 3 for mounting the fluid distributor (e.g., filter 103) to lower portion 15-2 of piston 15. This arrangement involves press-fitting a plurality of wedges 131 into annular slot 29 at various locations so that the fluid distributor can be supported upon wedges 131.

Another arrangement (not shown) for mounting the fluid distributor to piston 15 is to weld distributor directly to piston 15.

A preferred sterilization solution for use in sterilizing column 101 is an aqueous solution having a pH of about 5 and containing peracetic acid in a concentration of about 1500 mg/l to 5000 mg/l, an acetate buffer having a concentration of 0.5M and ethanol in a concentration of up to 40%.

The following experiment is included in the present application solely to demonstrate the operability of the present invention. This experiment is in no way intended to limit the scope of the present invention. Accordingly, the invention is best defined by the claims appended hereto.

Column Sterilization Experiment

Sterilization protocol—materials and pre-treatment:

All material used for the sterilization procedure with primary artificial contamination was sterilized, if possible, by wet heat (121° C., 30 min) to minimize cross contamination. Devices which allowed autoclaving were: Glass bottles (Schott, Wien, Austria), selectable with a lid construction containing through-passes for silicone tubes and de-aeration filters, silicone tubes i∅/o∅ 4/8 mm, connectors, T-pieces, Tri-clamp connections and Tri-clamp gaskets. Since chromatographic columns do not usually allow autoclaving they, or at least parts thereof, were pre-treated overnight with diluted peracetic acid (5000 ppm). All fluids (e.g., buffers 0.5M, pH 5, distilled water, Caso Bouillon) were autoclaved. Peracetic acid was added to the autoclaved buffer base, which was mainly sodium acetate 0.5N, pH 5.0. For liquid motion, an Ismatec SA peristaltic pump with a VP380 head was used.

Figure 12A:
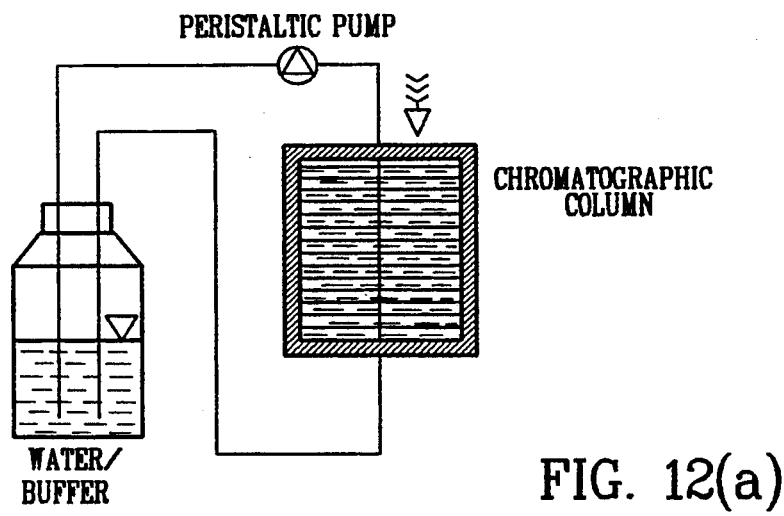
FIGS. 12(a) through 12(f) are a series of schematic diagrams illustrating the various steps of the sterilizing experiment to be described below.
Figure 12B:
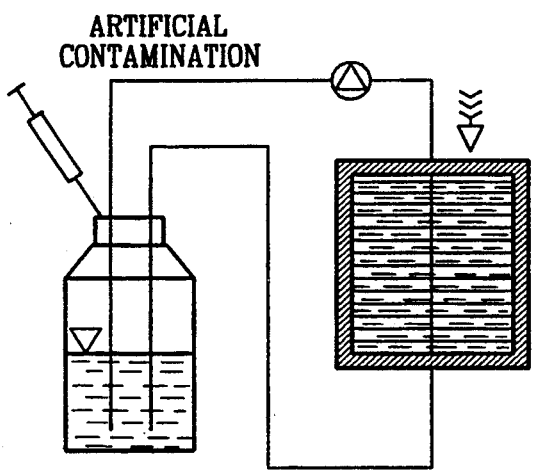
Figure 12C:
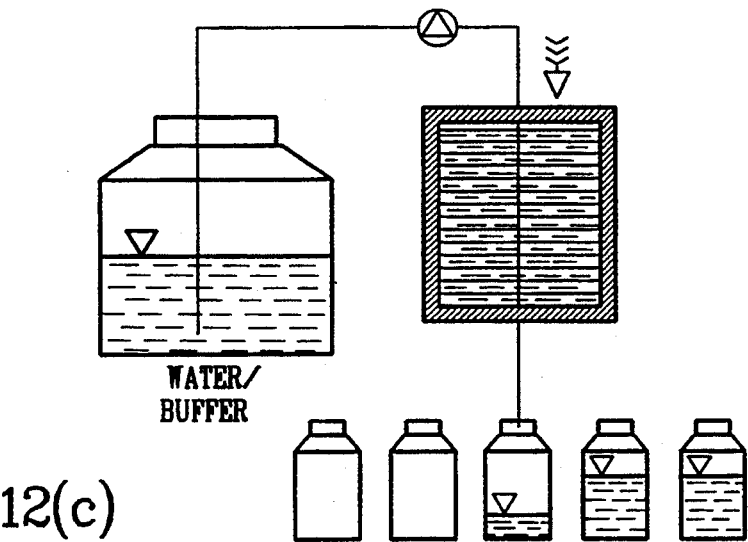

Sterilization protocol—experimental procedure:

First, the unpacked (or packed) column was filled with distilled water or buffer, and a certain volume calculated as the sum of silicone tubes, column volume and buffer reservoir was cycled (see FIG. 12(a)). Next, spores of $B.$ $subtilis$ were added to the circulating fluid to reach a spore density of approximately $10^{6\pm 0.5}$/ml (see FIG. 12(b)). After the artificial contamination, the fluid was cycled for at least 15 min to ensure uniform distribution of the spores throughout the whole system. The system was then washed with at least ten column volumes of distilled water or buffer (see FIG. 12(c)). The total volume of washing fluid was collected in a few fractions. The quantity of spores in each fraction was estimated by the agar plating method disclosed in Wallhäußer, "Sterilisation-Desinfektion Konservierung," 2nd Ed., Georg Thieme Verlag, p. 12, (1978), which is incorporated herein by reference.

Figure 12D:
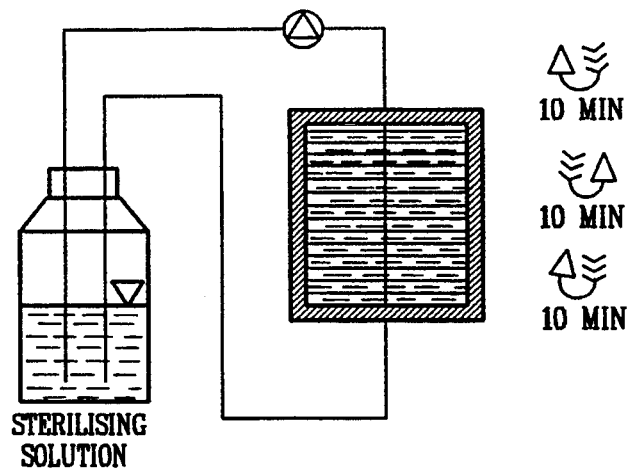
Figure 12E:
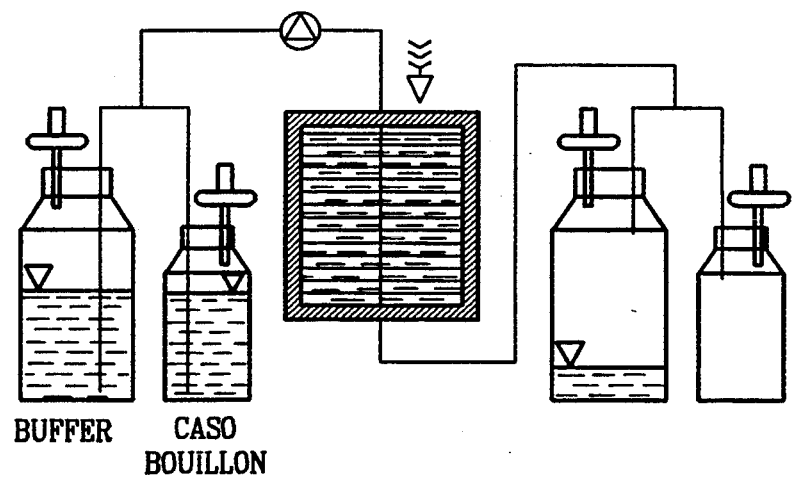

Next, two total column volumes (i.e., column volume plus silicone tubes) of decontamination solution were newly prepared. One column volume of decontamination solution was pumped through the column. The overflow was collected, a sample was drawn and its spore density was estimated. At this point onward, the remaining sterilization solution was cycled at a defined flow rate of 50 ml/min through the column. The direction of the fluid was then reversed at ten minute intervals (see FIG. 12(d)). By this treatment, the column and the silicone tubes should become sterilized. Sterility of the extremities of the silicone tubing was achieved by plunging them into the decontamination solution reservoir for the period of sterilization. After the sterilization period, a sample was drawn from the sterilization fluid to estimate the surviving germs. From this point onward, the experiment was carried out under aseptic conditions. The ends of the chemically sterilized silicone tube were connected aseptically to autoclaved inlet and outlet bottles. Two inlet and two outlet bottles were united by T-pieces. One inlet bottle was filled with four column volumes buffer, the other inlet bottle with two column volumes Caso bouillon. The joint end of the T-piece carried a silicone tubing piece and a connector. Since these ends had to be absolutely sterile (inner and outer sterility was recommended for the connector) before connecting them to the column-coupled, silicone-tubing extremities, it was necessary to wrap up the connector carrying the ends before autoclaving them with special autoclavable sacks. The sacks were cut, respectively "melted" off aseptically with a red hot blade and the connector ends were joined to the plunge sterilized silicone tubing ends of the column. The sterilisation solution was then displaced by pumping sterile buffer through the column into the outlet bottle. Following the buffer was Caso Bouillon, and its overflow collected at the outlet bottle (see FIG. 12(e)).

Figure 12F:
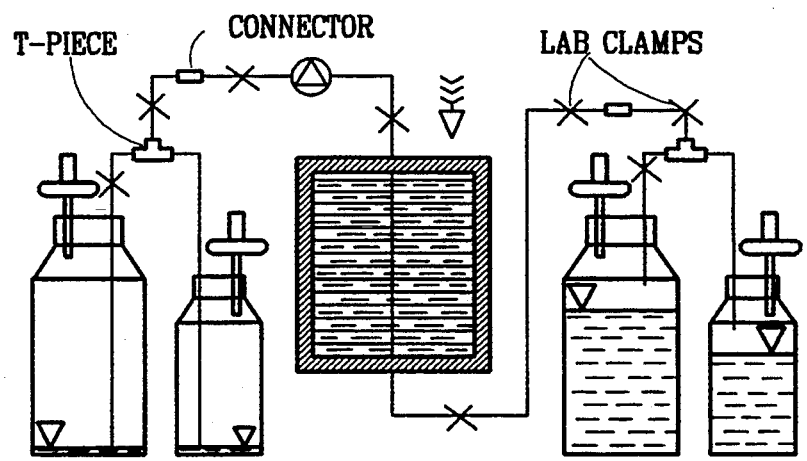

Sterilisation protocol—Evaluation of sterility:

The whole experimental set-up filled with Caso Bouillon was then incubated at 30° C. and observed for 7 days (see FIG. 12(f)). Turbidity of the Caso Bouillon was considered to be an unequivocal sign of microbial growth. Before incubation, the whole Caso Bouillon filled system was segmented with laboratory clamps, which serve as a barrier for microbial growth, so that the areas of both successful or poor chemical sterilisation could be determined. The following regions were segmented with laboratory clamps: a) inlet bottle-silicone tube-T-piece, b) silicone tube-connector-silicone tube, c) silicone tube, d) silicone tube-Tri-clamp-column-Tri-clamp-silicone tube e)=c, f)=b, g) outlet bottle-silicone tube-T-piece. If no turbidity was observed after seven days of incubation, sterility was considered to have been achieved.

In Table I below, there are summarized the results of sterilization experiments performed with chromatographic resins, the necessary peripheral devices for chromatographic column handling, and chromatographic columns itself. Sterility achieved means no detectable microbial growth in Caso Bouillon medium after seven days of incubation at 30° C.

TABLE I

| | DEVICE TO STERILIZE | STERILITY ACHIEVED |
|---|---|---|
| COLUMN PERIPHERY | | |
| 3 | SILICONE TUBE-CONNECTOR SYSTEM | YES |
| 4 | SILICONE TUBE-TRI-CLAMP SYSTEM | YES |
| 5 | POLYETHYLENE FRITS | YES/NO* |
| CHROMATOGRAPHIC COLUMNS (unpacked) | | |
| 6 | SEPRACOR UPSCALE ™ | NO |

TABLE I-continued

| | DEVICE TO STERILIZE | STERILITY ACHIEVED |
|---|---|---|
| | COLUMN ∅90 | |
| 7 | 6 WITHOUT ARTIFICIAL CONTAMINATION | NO |
| 8 | 6 WITHOUT POLYETHYLENE FRITS | NO |
| 9 | 6 WITHOUT O-RING, EXPANDING RING IN PISTON AND WITHOUT POLYETHYLENE FRITS | YES |
| 10 | 6 WITHOUT O-RING AND POLYETHYLENE FRITS BUT WITH EXPANDING RING | NO |
| 11 | PHARMACIA BIOPROCESS ™ 100/500 | NO |
| 12 | AMICON MODULINE ™ P70-250 | NO |
| 13 | MERCK SUPERPERFORMANCE ™ 500-50 | NO |

*The polyethylene frit in the piston cannot be sterilized by peracetic acid treatment after artificial contamination and washing procedure within the column, followed by disassembling of the frits and ex situ sterilizing procedure. This may be a consequence of massive enrichment of spores within the framework of the upper frit due to the pumping direction through the column. The bottom frit was successfully sterilized ex situ.

In line sterilization of packed column:

Sterilization of a column packed with a commercially available resin, i.e., Q-HyperD ™ chromatography resin (BioSepra, Inc., Marlborough, Mass.), was not possible. Although MPN (most probable number) estimates after the sterilizing procedure were very low (0 and 4 germs/100 ml), sterile conditions could not be achieved within the column. Table II below shows the germ contents during sanitization of a Sepracor UP-SCALE ™ column, ∅90, total system volume 0.415 l, packed with Q-HyperD ™ at a resin volume of 0.315 l, artificially contaminated with B. subtilis (1 l containing $2 \times 10^5$ colony forming units(cfu)/ml), using a washing solution (re-equilibration solution) with an acetate buffer 1M, pH 5.5 and a pump rate of 100 ml/min. After filling the packed column with Caso Bouillon and incubating at 30° C., bacterial growth could be detected within 24 hours.

TABLE II

| wash volume (l) | volume exchange | cfu/ml | cfu (total within the column) |
|---|---|---|---|
| 1 | 2.4 | $4 \times 10^2$ | $4.0 \times 10^5$ |
| 2 | 4.8 | $1.5 \times 10^2$ | $1.5 \times 10^5$ |
| 3 | 7.2 | $4.0 \times 10^1$ | $4.0 \times 10^4$ |
| 4 | 9.6 | $1.0 \times 10^1$ | $1.0 \times 10^4$ |
| 5 | 12.0 | $3.0 \times 10^1$ | $3.0 \times 10^4$ |
| PAA 0.5 | 13.3 | $2.1 \times 10^2$ | $1.1 \times 10^5$ |
| PAA 6.5 | 15.7 | 0 | 0 |
| PAA 7.5 | 18.1 | $4 \times 10^{-2}$ | $4 \times 10^1$ |

The sterilization procedure followed the same protocol described above.

Sterilization of a packed column:

The sterilization of packed columns was carried out following substantially the same procedure described above. The main differences are as follows: First of all, there was the packing of the column with the HyperD ™ resin. The matrix of the resin during packing included 20% ethanol, which had to be displaced by 0.5M acetate buffer, pH 5.0. As soon as the packed column was filled with acetate buffer, the system was ready for artificial contamination. Also, the washing step on packed columns was carried out using 1M acetate buffer. The use of this high molar buffer, which simulates reequilibration, is usually carried out before a new chromatographic run is started. Further, the sterilization step using 1500 ppm peracetic acid in 0.5M acetate buffer was prolonged to 60 minutes, and the flow direction was changed after each 20 minutes. In addition, the peracetic acid replacement was carried out with two liters of sterile PBS-buffer. Two fractions, one liter each, were collected and a MPN (most probable number) estimation of each fraction was accomplished.

The reasons why the sterilization of chromatographic columns and the asepsis of chromatographic processes are not typically attainable are dead ends within the columns. Sterility, which is an unequivocal expression describing the state when no viable microorganism exists within a system, cannot really be achieved. Only statistical germ contents can be given from the effluent liquid, expressed as a probability measured by MPN estimates.

Example 1

Sterilizing protocol of chromatographic column using a NaOCl solution (500 ppm free chlorine, pH 8.5)

The experiment procedure followed the experimental protocol written above. A chromatographic embodiment based on a Sepracor Chromatographic Upscale TM ⌀90 column was used, the column being modified to include, instead of the conventional polyethylene frit and expanding ring combination, a FUJIPLATE filter and a corrugated expanding ring. The column had a system volume of 0.5 liter, without resin, and was filled with distilled water. The column system was then artificially contaminated by spores of B. subtilis at a density of $1.16 \times 10^6$ cfu/ml. After challenging the column, the spores were washed out by pumping (flow rate 100 ml/min) 5 liters of distilled water through the column. About 98% of the initial germ content in the column was washed out by this treatment. Subsequently, 0.5 liter of the hypochlorite solution (500 ppm free chlorine, pH 8.5) was pumped through the column. A second portion of 500 ml sanitization solution was recycled in the column for a period of 180 min at a defined flow rate of 100 ml/min. The flow direction was changed after each 60 minutes.

After the contact time of 180 min, sterile NaCl buffer and Caso Bouillon were connected aseptically onto the column and the hypochlorite solution was displaced by pumping 5 liters of sterile 0.5M NaCl through the column. Next, the NaCl was displaced by Caso Bouillon and the column was filled with Caso Bouillon and incubated at 30° C. for seven days.

After seven days, no microbial growth could be detected.

Example 2

Sterilizing protocol using peracetic acid solution (peracetic acid 1500 ppm, acetate buffer 0.5M, pH 5)

The experiment procedure followed the experimental protocol written above. The same type of column used in Example 1 was used again and was filled with distilled water. The column system was then artificially contaminated by spores of B. subtilis at a density of $1.37 \times 10^6$ cfu/ml. After challenging the column, the spores were washed out by pumping, at a flow rate of 100 ml/min, 5 liters of distilled water through the column. About 98% of the initial germ content in the column was washed out by this treatment. Subsequently, 0.5 liter of the peracetic acid based sanitizing solution (1500 ppm peracetic acid, 0.5M acetate buffer, pH 5) was pumped through the column. A second portion of 500 ml sanitization solution was recycled in the column for a period of 30 min at a defined flow rate of 100 ml/min. The flow direction was changed after each 10 minutes.

Example 3

Figure 1:
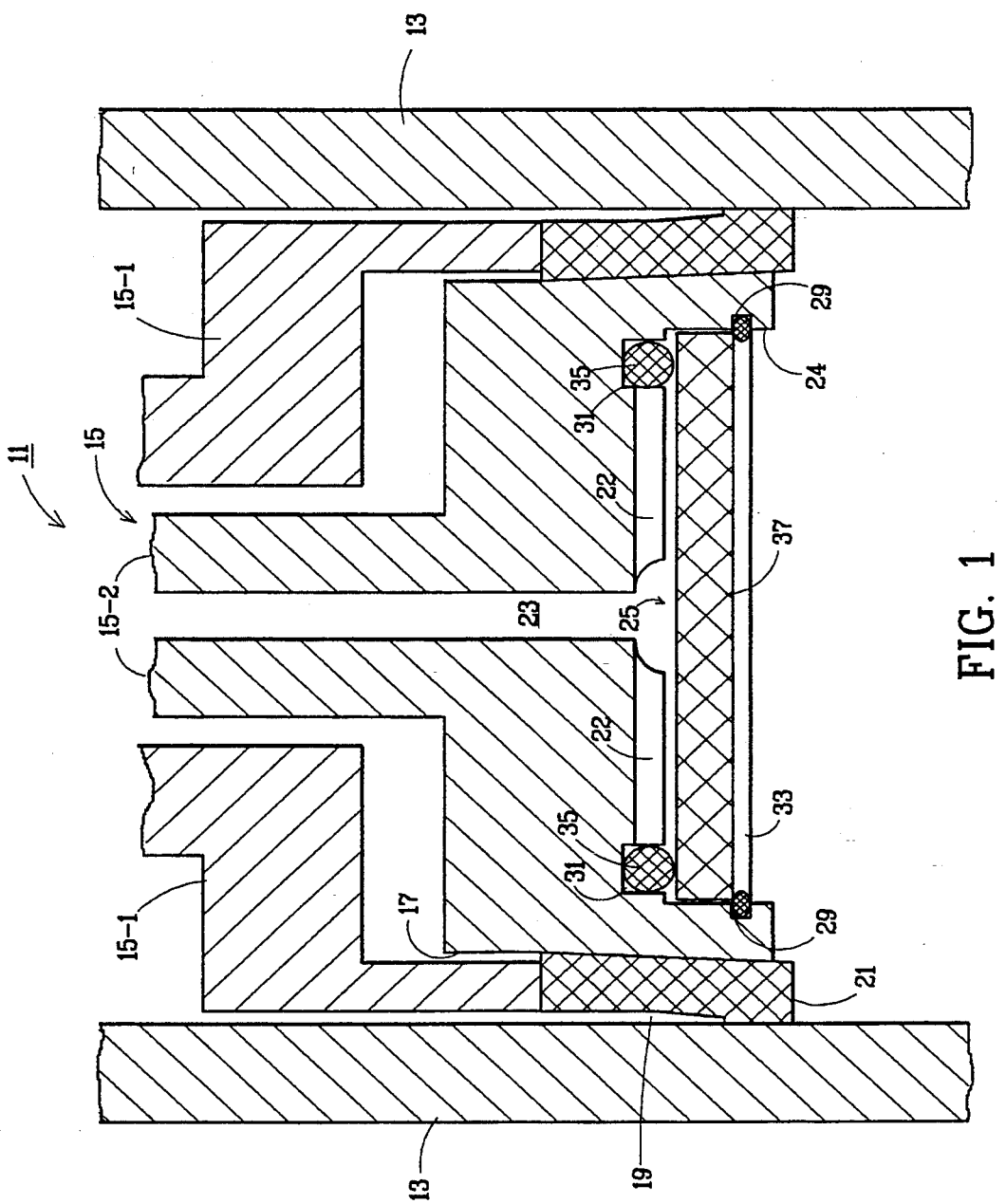
FIG. 1 is a fragmentary, simplified, schematic, section view of a first type of conventional liquid chromatography column.
Figure 2:
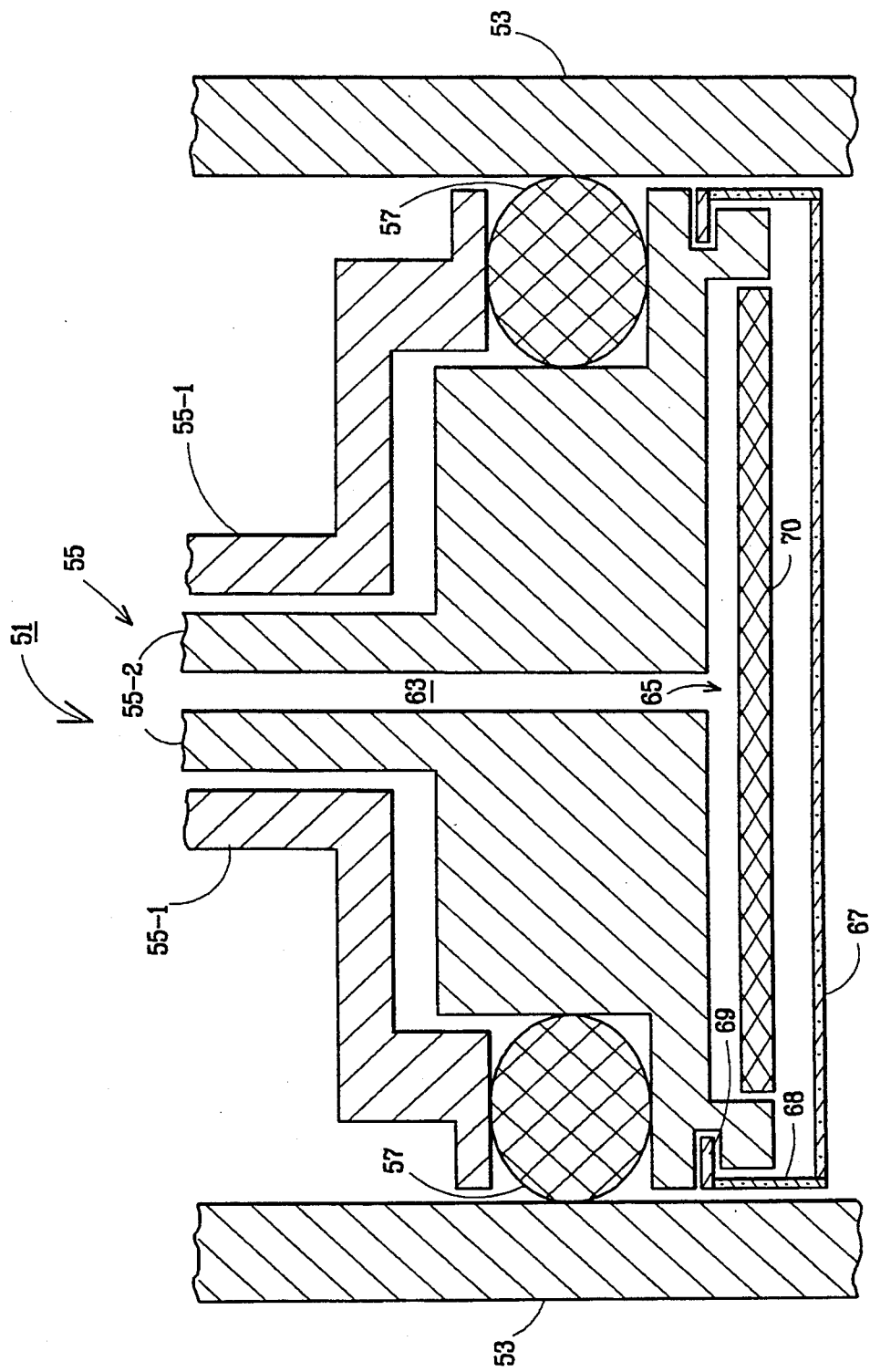
FIG. 2 is a fragmentary, simplified, schematic, section view of a second type of conventional liquid chromatography column.

Comparison of chromatographic performance of a conventional column and a column of the present invention suited for in-situ sterilization A chromatography column (Sepracor UPSCALE TM ⌀90) representing a conventional construction as shown in FIG. 1, was packed with Q-HyperD TM resin. The bed height was 11 cm. The column was equilibrated with 10 mM Tris HCl buffer, pH 8.0. The column was connected to a Biopilot System (Pharmacia Biotechnology, Uppsala, Sweden) and operated at a flow rate of 75 ml/min corresponding to 86 cm/h. The column outlet was connected to a conductivity monitor. The signal was acquired by a chromatography data acquisition system from Nelson Analytical (Cupertino, Calif.). After equilibration a pulse of 1 ml 1M NaCl solution (in 10 mM Tris HCl, pH 8.0) was applied onto the column. The column was operated until the NaCl was eluted from the column. As a measure of performance, HETP (i.e., height equivalent to one theoretical plate) was calculated.

$$HETP = L/N = L[\sigma/t_R]^2$$

wherein N is the number of plates, L is the column length, $t_R$ is the retention time and $\sigma$ is the peak variance. The data were attained from the chromatography data acquisition system. HETP for the conventional column was estimated to be in the range of 11/90 (i.e., 0.122 cm).

The HETP performance of a chromatographic column of the type having the arrangement shown in FIG. 11 was evaluated as well. The column packing, equilibration and sample application were carried out in the same manner described above. The values for $t_R$ were measured and calculated. HETP for this column was in the range of 10.5/90 (i.e., 0.117 cm).

Consequently, one can conclude that the chromatographic performances of the two columns do not differ significantly.

The embodiments of the present invention recited herein are intended to be merely exemplary and those skilled in the art will be able to make numerous variations and modifications to them without departing from the spirit of the present invention. For example, the principles of the present invention could be applied to chromatographic techniques employing either fixed or fluidized beds. In addition, the distributors of the present invention could be made from material(s) other than metals, such as a polymeric material which provides a defined mesh. Furthermore, a separate diffuser, mounted below the distributor, could be added to the column to improve fluid distribution. These and all such variations and modifications are intended to be within the scope of the present invention as defined by the claims appended hereto.

What is claimed is:

1. A liquid chromatography column comprising:
   (a) a liquid chromatography tube packed with a liquid chromatography resin;

(b) a piston assembly mounted within said liquid chromatography tube towards the upper end thereof, said piston assembly including an upper portion and a lower portion, said lower portion being shaped to include a fluid distribution channel and a downwardly-extending collar, said downwardly-extending collar including an annular slot and defining an orifice in fluid communication with said fluid distribution channel;

(c) a distributor disposed within said orifice for distributing fluid conducted through said fluid distribution channel over the entirety of said orifice, said distributor being positioned over said liquid chromatography resin; and (d) means for mounting said distributor within said orifice, said mounting means comprising a corrugated expanding ring mounted in said annular slot, said corrugated expanding ring supporting said distributor.

2. The liquid chromatography column as claimed in claim 1 wherein said distributor is a multilayer sintered metal filter of defined mesh.

3. The liquid chromatography column as claimed in claim 1 wherein said distributor is a metal plate, said metal plate having a plurality of perforations, said perforations having a hole diameter less than the lower grain diameter of said liquid chromatography resin.

4. The liquid chromatography column as claimed in claim 3 wherein said metal plate is a plate of stainless steel and wherein said perforations have a hole diameter of about 0.5 to 200 $\mu$m.

5. The liquid chromatography column as claimed in claim 1 wherein said distributor is a woven and/or sintered stainless steel monolayer welded onto a metal ring.

6. The liquid chromatography column as claimed in claim 1 wherein an annular space is formed between said chromatography tube and the outer periphery of said lower portion of said piston, said liquid chromatography column further comprising a sealing ring for sealing off said annular space.

7. A liquid chromatography column comprising:

(a) a liquid chromatography tube packed with a liquid chromatography resin;

(b) a piston assembly mounted within said liquid chromatography tube towards the upper end thereof, said piston assembly including an upper portion and a lower portion, said lower portion being shaped to include a fluid distribution channel and a downwardly-extending collar, said downwardly-extending collar including an annular slot and defining an orifice in fluid communication with said fluid distribution channel;

(c) a distributor disposed within said orifice for distributing fluid conducted through said fluid distribution channel over the entirety of said orifice, said distributor being positioned over said liquid chromatography resin; and (d) means for mounting said distributor within said orifice, said mounting means comprising a plurality of wedges press-fitted into said annular slot, said plurality of wedges supporting said distributor.

8. The liquid chromatography column as claimed in claim 7 wherein said distributor is a multilayer sintered metal filter of defined mesh.

9. The liquid chromatography column as claimed in claim 7 wherein said distributor is a metal plate, said metal plate having a plurality of perforations, said perforations having a hole diameter less than the lower grain diameter of said liquid chromatography resin.

10. The liquid chromatography column as claimed in claim 9 wherein said metal plate is a plate of stainless steel and wherein said perforations have a hole diameter of about 0.5 to 200 $\mu$m.

11. The liquid chromatography column as claimed in claim 7 wherein said distributor is a woven and/or sintered stainless steel monolayer welded onto a metal ring.

* * * * *